(12) United States Patent
Haidekker et al.

(10) Patent No.: US 7,943,390 B2
(45) Date of Patent: May 17, 2011

(54) SUPPORTED MOLECULAR BIOFLUID VISCOSITY SENSORS FOR IN VITRO AND IN VIVO USE

(75) Inventors: Mark A. Haidekker, Columbia, MO (US); Sheila Grant, Columbia, MO (US); Emmanuel Theodorakis, San Diego, CA (US); Marcos Intaglietta, La Jolla, CA (US); John A. Frangos, La Jolla, CA (US)

(73) Assignees: The Curators of the University of Missouri, Columbia, MO (US); The Regents of the University of California, Oakland, CA (US); La Jolla Bioengineering Institute, La Jolla, CA (US)

( * ) Notice: Subject to any disclaimer, the term of this patent is extended or adjusted under 35 U.S.C. 154(b) by 11 days.

(21) Appl. No.: 12/426,653

(22) Filed: Apr. 20, 2009

(65) Prior Publication Data

US 2009/0227880 A1    Sep. 10, 2009

Related U.S. Application Data

(62) Division of application No. 11/039,076, filed on Jan. 20, 2005, now Pat. No. 7,670,844.

(60) Provisional application No. 60/537,679, filed on Jan. 20, 2004.

(51) Int. Cl.
*G01N 33/00* (2006.01)
(52) U.S. Cl. .... 436/148; 422/50; 422/82.05; 422/82.06; 422/82.07; 422/82.09
(58) Field of Classification Search .................. 436/148; 422/50, 82.05, 82.06, 820.7, 82.09
See application file for complete search history.

(56) References Cited

U.S. PATENT DOCUMENTS

| 5,384,079 | A | 1/1995 | Bur et al. |
| 6,531,097 | B1 | 3/2003 | Vojnovic et al. |
| 7,517,695 | B2 * | 4/2009 | Haidekker .................... 436/172 |

FOREIGN PATENT DOCUMENTS

WO    WO 02/086471    10/2002

OTHER PUBLICATIONS

Akers et al., "Precision Assessment of Biofluid Viscosity Measurements Using Molecular Rotors", *Journal of Biomechanical Engineering*, vol. 127, Jun. 2005, pp. 450-454.

Haidekker et al., "A Novel Approach to Blood Plasma Viscosity Measurement Using Fluorescent Molecular Rotors", *American Journal of Physiology—Heart and Circulatory Physiology*, vol. 282, 2002, pp. H1609-H1614.

Kung et al. "Fluorescent Molecular Rotors: A New Class of Probes for Tubulin Structure and Assembly", *Biochemistry*, vol. 1989, No. 28, Sep. 21, 1988, pp. 6678-6686.

Loutfy et al., "Effect of Viscosity and Temperature on Torsional Relaxation of Molecular Rotors", *J. Phys. Chem.*, vol. No. 86, No. 21, 1982, pp. 4205-4211.

* cited by examiner

*Primary Examiner* — Sam P Siefke
(74) *Attorney, Agent, or Firm* — Greer, Burns & Crain Ltd.

(57) ABSTRACT

A device and a method for measuring viscosity that includes attaching molecular rotors to a solid surface, exposing the solid surface to a fluid having a viscosity to be measured, and taking optical measurements to determine viscosity. The solid surface is preferably quartz, polystyrene or silicate glass, such as a fiber optic probe or a glass cuvette. The molecular rotors are of the type that includes an electron-donor group and electron-acceptor group that are linked by a single bond so that the groups may rotate with respect to one another, and that exhibit a fluorescence emission when rotation is hindered.

23 Claims, 21 Drawing Sheets

SCHEME 2. GENERAL SYNTHESIS OF MOLECULAR ROTORS BOUND ON GLASS SUPPORT

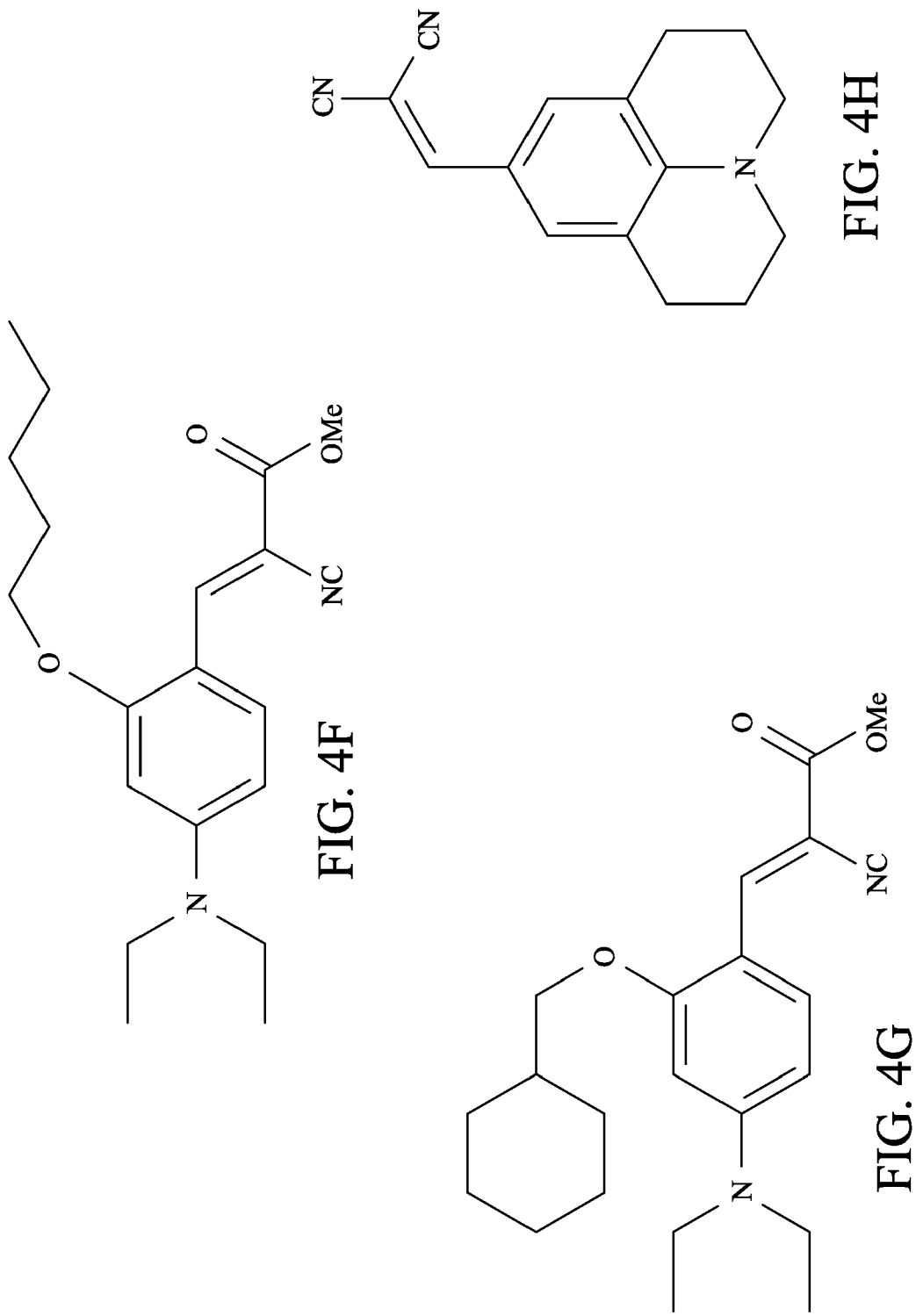

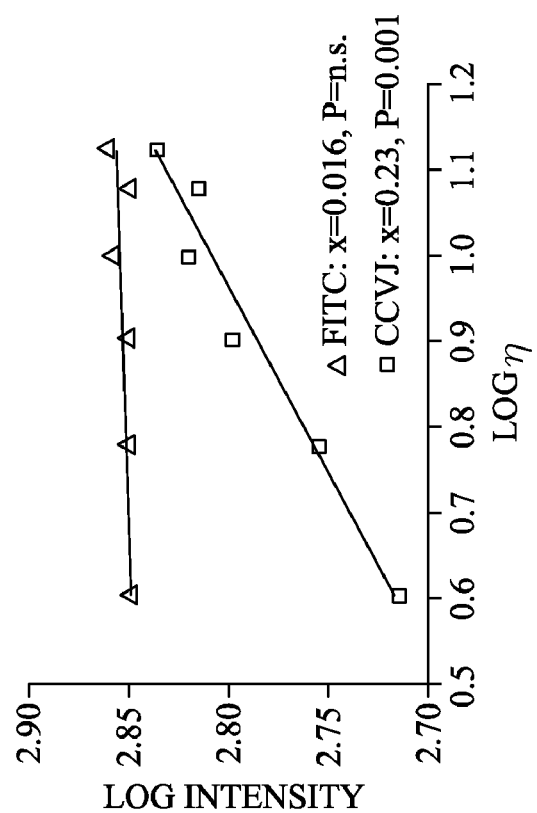
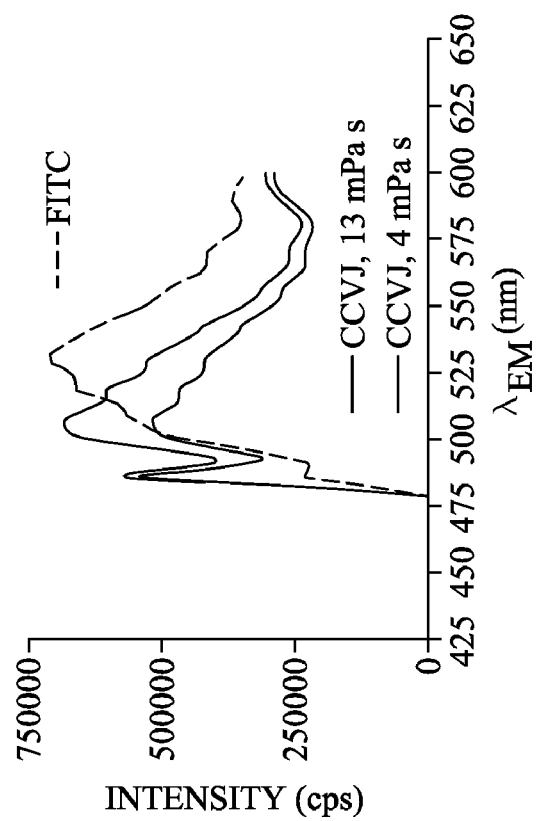
FIG. 7B
FIG. 7A

| SAMPLE SET | PLASMA (ml) | EXPANDER (ml) | PRESTAINED PLASMA (ml) |
|---|---|---|---|
| 1 | 4 | 0 | 1 |
| 2 | 3 | 1 | 1 |
| 3 | 2 | 2 | 1 |
| 4 | 1 | 3 | 1 |
| 5 | 0 | 4 | 1 |

FIG. 8

| PLASMA EXPANDER | K | V | MAX DEVIATION |
|---|---|---|---|
| HETASTARCH (6%) | 0.00491 | 0.6390 | 4.9% |
| PENTASTARCH (10%) | 0.00360 | 0.7030 | 5.03% |
| DEXTRAN (5%) | 0.00315 | 0.4542 | 3.75% |

FIG. 14

| PLASMA EXPANDER | K | V | MAX DEVIATION |
|---|---|---|---|
| HETASTARCH (6%) | 0.00130 | 0.9684 | 5.48% |
| PENTASTARCH (10%) | 0.00369 | 0.6959 | 3.20% |
| DEXTRAN (5%) | 0.00279 | 0.4391 | 1.32% |

FIG. 15

| VISCOSITY | MECHANICAL COEFFICIENT OF VARIATION | CCVJ FLUORESCENCE COEFFICIENT OF VARIATION | CCVJ-TEG FLUORESCENCE COEFFICIENT OF VARIATION |
|---|---|---|---|
| 1.78 | 0.087 | 0.050 | 0.034 |
| 2.13 | 0.074 | 0.024 | 0.025 |
| 2.50 | 0.046 | 0.019 | 0.091 |
| 3.13 | 0.068 | 0.036 | 0.022 |
| 3.75 | 0.070 | 0.042 | 0.017 |

FIG. 16

SUPPORTED MOLECULAR BIOFLUID VISCOSITY SENSORS FOR IN VITRO AND IN VIVO USE

CROSS-REFERENCE TO RELATED APPLICATION

Pursuant to 35 U.S.C. §119(e), this application is entitled to the benefit of U.S. Provisional Application Ser. No. 60/537,679, filed Jan. 20, 2004. This application is a divisional of U.S. Ser. No. 11/039,076, filed Jan. 20, 2005.

STATEMENT OF GOVERNMENT INTEREST

This invention was made with Government support under Contract Numbers NIH 1R21 RR018399, NIH HL062354, and NIH R01 HL040696 awarded by the National Institutes of Health. The Government has certain rights in the invention.

FIELD OF THE INVENTION

A field of the invention is biofluid analysis. Other exemplary fields of the invention include medical diagnosis, medical test systems, and medical laboratory processes.

BACKGROUND OF THE INVENTION

Blood and blood plasma viscosity may become abnormal due to a variety of pathologic conditions. While the viscosity of full blood is primarily determined through hematocrit, changes in viscosity are observed in conjunction with various diseases, primarily those associated with altered protein levels. For example, infection, infarction, hypertension, or diabetes may alter plasma viscosity, which in turn may complicate the condition. Protein-induced hyperviscosity may lead to an elevated risk of atherosclerosis. Additionally, one of the adverse effects of smoking is elevated plasma viscosity, which may be the link between cigarette consumption and cardiovascular disease.

Non-pathogenic conditions may also influence blood rheology, including bed rest (e.g., associated with prosthetic implants), pregnancy and aging. Viscosity changes during the aging process may also be attributed to indirect effects, such as age-related changes in habits (e.g., increased smoking or lack of exercise).

Accordingly, using plasma viscosity as a diagnostic tool to allow early detection of diseases is advantageous. Even where there is no direct causal relationship between disease and plasma viscosity, measurement of plasma viscosity nonetheless becomes a crucial element in sever hemorrhage when hemodilution leads to dramatically lowered hematocrit and plasma viscosity plays an important role. Blood expansion with high-viscosity fluids enhances capillary perfusion and thus tissue oxygenation.

Accordingly, for many related purposes, including viscosity-related research, diagnosis of cardiovascular disease, or monitoring of the blood resuscitation process, a viscometer that is capable of fast serial measurement with low volumes is desirable. Mechanical devices for the measurement of fluid viscosity are presently available, but they continue to pose disadvantages such as slow measurements, lack of robustness, the need for meticulous cleaning and susceptibility to operator errors. The most widely used conventional mechanical devices are: the falling-ball viscometers (wherein the time required to produce a result usually measures from between 1 minute and 20 minutes), which have high susceptibility toward uncleanliness and the occurrence of solid particles or air in the fluid; flow-resistance viscometers, such as capillary or Oswald-type viscometers, which need high volumes of fluid and require measurement times in the order of minutes; and cone-and-plate viscometers, which have the same disadvantages of the flow-resistance viscometers.

Additionally, a class of molecules known as molecular rotors have been used to probe fluid viscosity in vitro. Molecular rotors are fluorescent molecules with a quantum yield that is dependent on the free volume—and thus the viscosity—of their environment. Molecular rotors form a twisted internal charge transfer (TICT) complex upon excitation. These molecules have a preferred de-excitation pathway of internal conversion through rotation about a C=C double bond. This internal rotation rate depends on the viscosity of the solvent, leading to a viscosity-dependent quantum yield. For example, 9-(2,2-dicyanovinyl)-julolidine (DCVJ) has been used to probe fluid viscosity in vitro by dissolving the DCVJ in a fluid having a viscosity to be measured, and subsequently observing the fluorescence emission. However, because the rotors are dissolved in the fluid to be observed, the applications are limited to in vitro applications.

SUMMARY OF THE INVENTION

The instant invention is directed to viscosity sensors for both in vitro and in vivo applications, and is more specifically directed to the use of molecular rotors disposed on a solid surface for use as a viscosity probe for in vivo applications as well as in vitro applications. In a particular embodiment of the invention, a fiber optic tip has molecular rotors adhered to it. The tip may be shaped and sized, for example, to be inserted into animal or human vessels having a predetermined circumference. The fiber optic tip may form the end of an optical waveguide that can guide both excitation light and responsive emissions for viscosity testing. The responsive emissions are analyzed for example by a computer that determines viscosity values based upon the acquired responsive emissions.

Another embodiment of the invention includes adhering molecular rotors to one or more walls of a glass receptacle, which may then be filled with a fluid having a viscosity to be measured. Measuring the fluorescence emission from the receptacle-bound molecular rotors is indicative of viscosity.

DESCRIPTION OF THE DRAWINGS

FIGS. 4A, 4B, 4C, 4D, 4E, 4F, 4G and 4H are structures of exemplary molecular rotors that may be used with the invention;

FIGS. 7A and 7B are graphs showing two representative CCVJ spectra in low-viscosity and high-viscosity fluid (4 mPa s and 13.35 mPa s, respectively) with the fluorescein spectrum as a control;

FIG. 8 is a table illustrating a calibration set consisting of 5 replicates of 5 plasma-plasma expander ratios with 13.3 µM dye;

FIG. 14 is a table illustrating constants of Equation 2 for CCVJ in plasma-plasma expander mixtures with maximum deviation;

FIG. 15 is a table of constants for Equation 2 for CCVJ-TEG in plasma-plasma expander mixtures with maximum deviation;

FIG. 16 is a table illustrating a comparison of coefficients of variation of mechanical and fluorescence viscosity measurements of plasma-hetastarch mixtures with CCVJ and CCJV-TEG.

DETAILED DESCRIPTION OF THE INVENTION

Molecular rotors are fluorescent molecules with a quantum yield that is dependent on the free volume—and thus the viscosity—of their environment. Molecular rotors form a twisted internal charge transfer (TICT) complex upon excitation. These molecules have a preferred de-excitation pathway of internal conversion through rotation about a C=C double bond. This internal rotation rate depends on the viscosity of the solvent, leading to a viscosity-dependent quantum yield.

Molecular rotors have been successfully used to probe cell membrane viscosity and blood plasma viscosity in vitro. However, measurement requires that a defined amount of the fluorescent dye (the molecular rotor material) be dissolved in a sample fluid at known concentrations. Variations in dye concentration, different light absorption coefficients of the measured fluid as well as turbidity of the fluids needs to be compensated for. In addition, a molecular rotor that needs to be dissolved in the fluid is precluded from in vivo measurements, which prevents their use in viscosity analyses of biofluids such as blood plasma.

Embodiments of the invention provide for molecular rotors that are placed on a solid surface, such as any glass or polymer substrate that may be pre-functionalized (e.g., quartz, polystyrene or silicate glass) to create a probe that may then be used for in vivo as well as in vitro viscosity measurements. Such a probe has virtually unlimited potential for viscosity measurement applications, for example either in vivo or in vitro biofluid viscosity monitoring and measurement, industrial viscosity monitoring (e.g., in the food industry), organic solvents, aqueous solutions, and aqueous colloid solutions (e.g., the food and/or soft drink industry).

For example, in a first preferred embodiment, molecular rotors are adhered to a fiber optic probe, which may then be used as an in vivo probe of blood or biofluid viscosity via fluorescence intensity measurements. In a second preferred embodiment, molecular rotors are adhered to one or more walls of a glass cuvette, and once the cuvette is filled with a sample, the viscosity of a boundary layer of the fluid in the cuvette can be measured via fluorescence intensity measurements. In both preferred embodiments, the molecular rotors are covalently bound to the solid surface. Additionally, while the invention contemplates inclusion of a virtually unlimited number of molecular rotors, several exemplary molecular rotors will be shown and described.

Figure 1B:
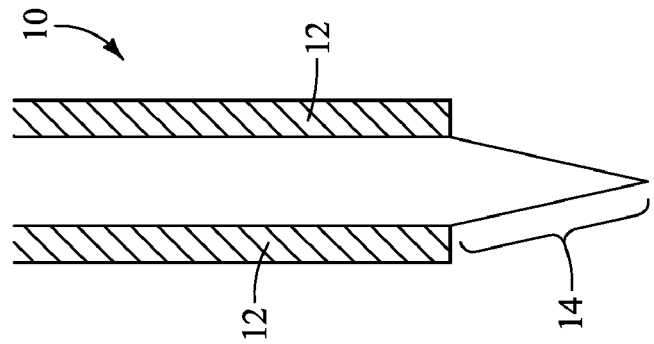
FIGS. 1A and 1B are schematic diagrams illustrating solid-bound molecular rotors applied to a fiber optic tip.
Figure 1A:
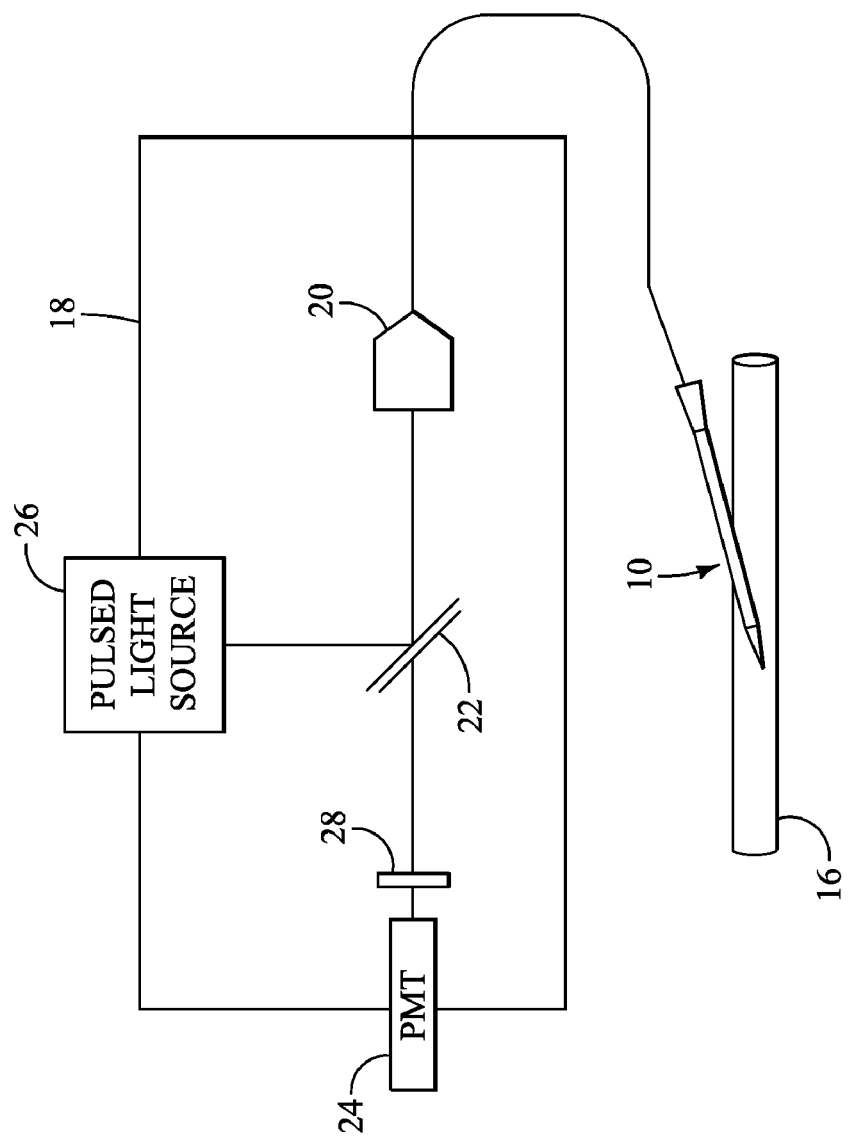

Rotor-Covered Fiber Optic Probe for In Vivo Measurements:

A device for in vivo use is shown in FIGS. 1A and 1B, which are schematic diagrams illustrating solid-bound molecular rotors applied to a tip of a fiber optic probe fiber optic tip. The fiber optic probe, designated generally at 10, is preferably enclosed within a polymer coating or plastic cover 12, except for a tip portion 14 that is to be covered with molecular rotors and intended to be inserted into a blood vessel 16 or other tube. The fiber optic probe 10 is preferably coupled to a light-proof encasing 18, which houses a fiberoptic coupling device 20 and a dichroic mirror 22. A photomultiplier tube 24 is provided, as is a pulsed light source 26. A longpass filter 28 is also preferably provided. The tip 14 is preferably etched in hydrofluoric acid to obtain a larger surface area, and the rotors are attached according to FIG. 2. While immobilization may occur via any conventional method known in the art, one possible immobilization process would briefly include the following steps:

(a) etch a new tip on the fiber optic with hydrofluoric acid 40% solution, approximately 4 hours total, rinse in distilled water. Peel away the polymer coating to expose the tip using a razor blade and remove the cladding.

(b) wash tip in hydrochloric acid and methanol, then in sulfuric acid. Rinse and dry.

(c) sonicate tip for 6 to 8 minutes in 5% solution (v/v) of 3-aminopropyl-triethoxysilane (ABS from Signam cat no. A-3646) in absolute ethanol.

(d) bake the fiber tip for 1 minute at 120 degrees C.

(e) prepare working solution of 9-(2-carboxy-2-cyanovinyl)-julolidine-NHS (CCVJ-NHS) in 50 mM sodium bicarbonate solution pH 8.5, the final concentration of dye is 0.1 μg/μl with 10% DMSO present.

(f) incubate the tip of the fiber optic in the working solution of CCVJ-NHS for at least 1 hour. Sonicate in DMSO to remove excess dye.

The tip may be catheterized and inserted into blood vessels in vivo. Due to the low incidence angle, excitation light is refracted out of the tip, and problems with reflected or scattered incident light are expected to be minimized. Additionally, a pulsed light source in combination with gated signal acquisition will be used to reduce influences of environmental light. Thus, a patient with a probe inserted does not need to stay in a low-light environment. The tip is also preferably autoclaved for sterility.

Fluorescent molecular rotors belong to the group of twisted intramolecular charge-transfer complexes that possess free rotary vinyl groups in their molecules. Each molecular rotor is composed of two subgroups, which include an electron-donor group and an electron acceptor group. Both groups are linked by at least one single bond, so that the two groups are able to rotate freely against each other. Photoexcitation leads to an electron transfer from a donor group to an acceptor group. Relaxation can either occur through radiation (fluorescence) or intramolecular rotation (thermally induced non-fluorescent relaxation). The preferred relaxation mechanism, intramolecular rotation, is reduced in solvents with low free volume. Therefore, the quantum yield of a molecular rotor increases with decreasing free volume of the solvent. Free volume and viscosity are related, which links quantum yield directly to the viscosity of the microenvironment. The relationship between fluorescence quantum yield ($\Phi$) and the viscosity (η) of the solvent has been derived analytically and experimentally and is known as the Förster-Hoffmann equation:

$$\log \Phi = C + x \log \eta$$

Thus, a virtually unlimited number of molecular rotors may be used in conjunction with the instant invention. For example, several exemplary acceptor groups include any motif that contains an OH, CN, COOH or its carboxylic esters and amides, such as esters of n-ethylene glycol attached to a vinyl (C=C), while several exemplary donor groups include an N atom that is not bound in a cyano (CN) manner, such as julolidine and amino-benzenes. The "opened" structures and the three julolidine rings are especially advantageous.

For the instant embodiment as well as additional embodiments discussed herein, it is anticipated that derivation of quantum yield may be obtained via both lifetime measurement as well as continuous-wave fluorescence. As illustrated by the Förster-Hoffmann-equation, viscosity and quantum yield are related, so measurement of quantum yield is desirable. In addition to being proportional to quantum yield, emission intensity also depends on excited-state lifetime, from which quantum yield may be computed. Thus, using advanced instrumentation capable of lifetime measurement, quantum yield may be measured via lifetime analysis as well as via continuous-wave fluorescence.

Figure 3B:
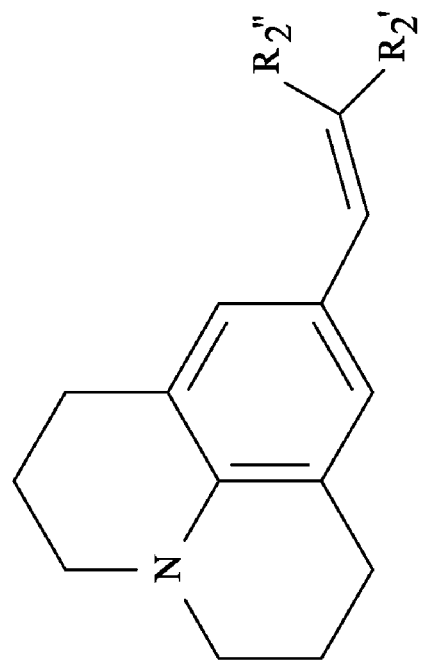
FIGS. 3A, 3B, 3C, 3D, 3E and 3F illustrate structures of exemplary rotors.
Figure 3A:
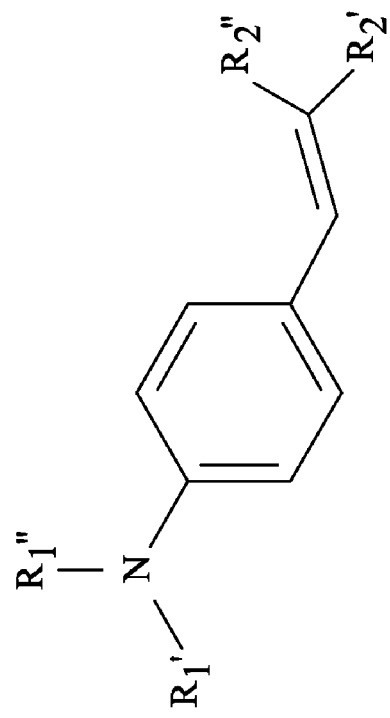
Figure 3C:
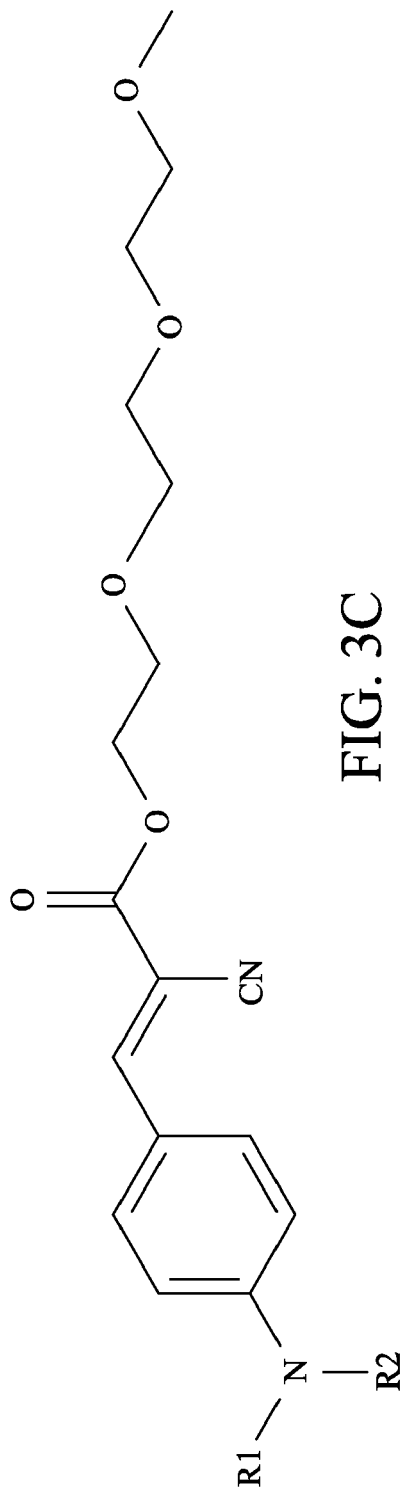
Figure 3D:
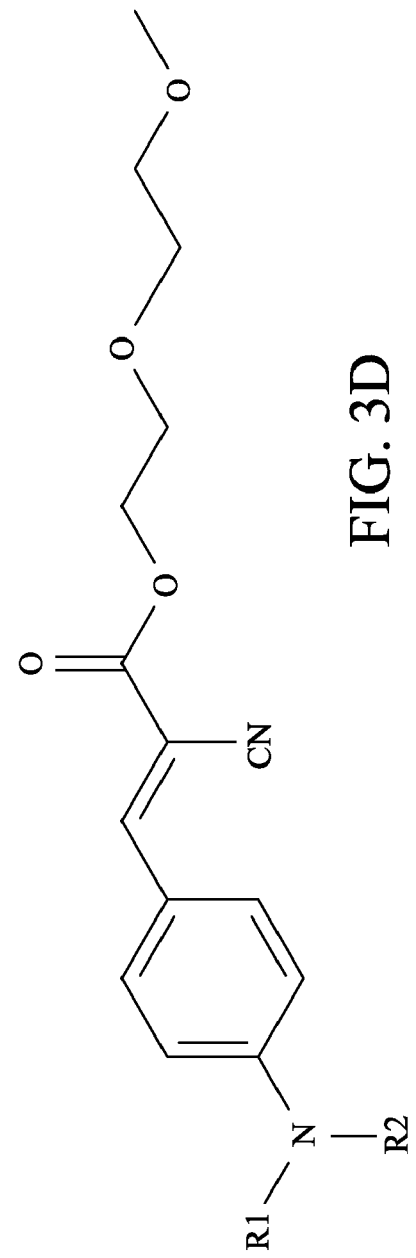
Figure 3E:
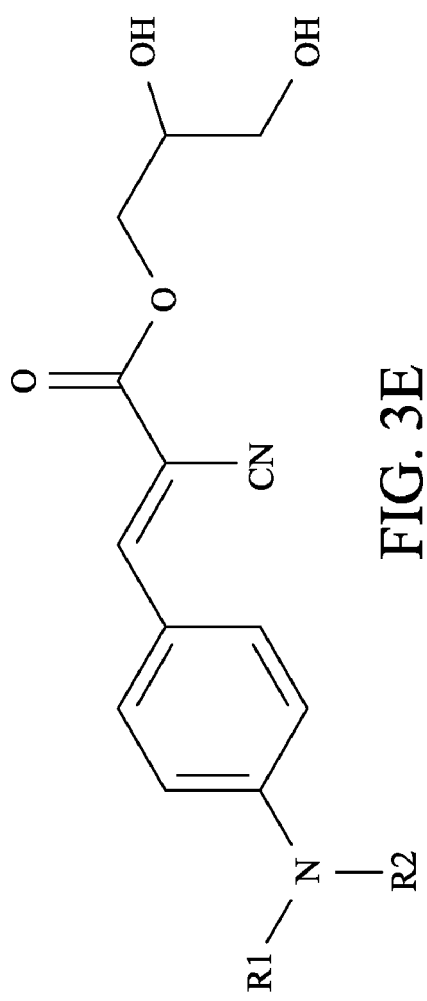
Figure 3F:
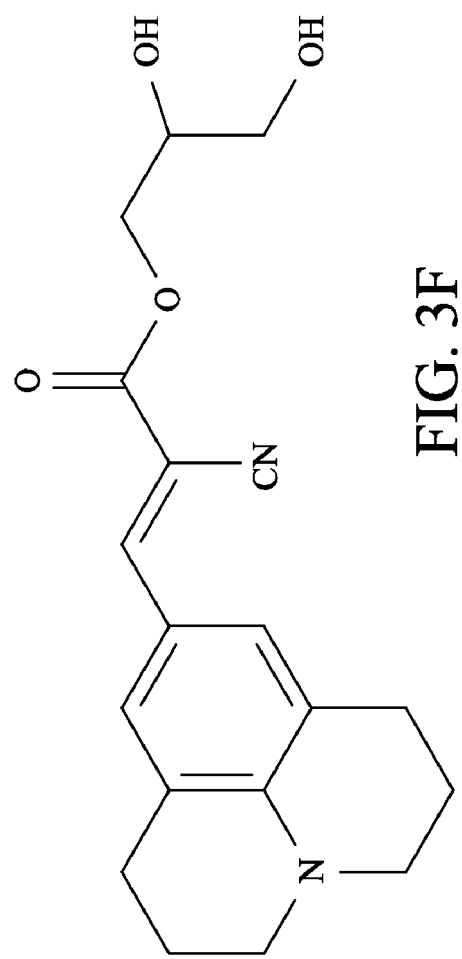
Figure 4B:
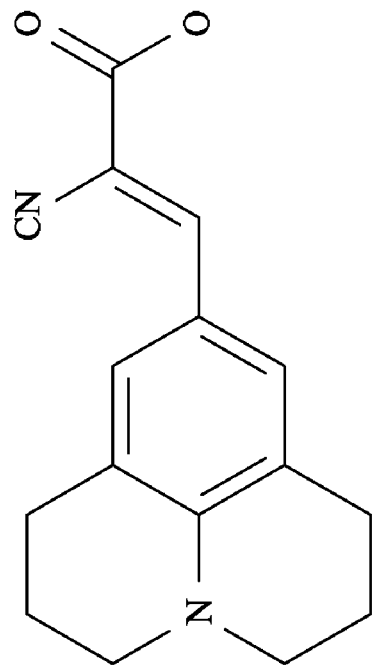
Figure 4A:
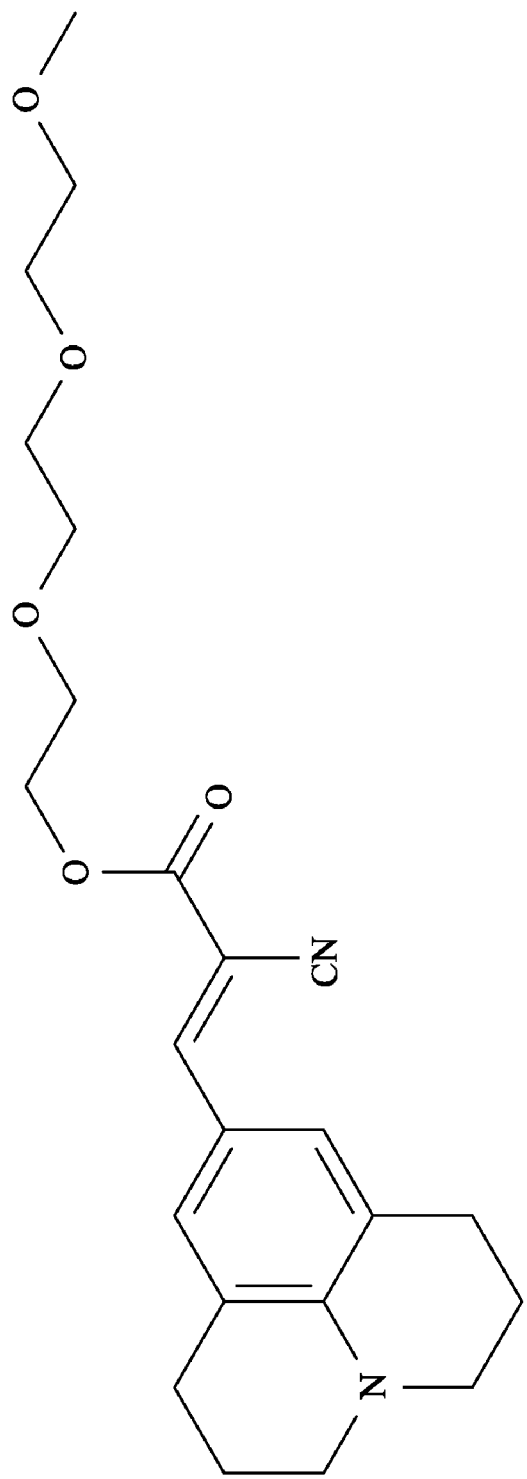
Figure 4E:
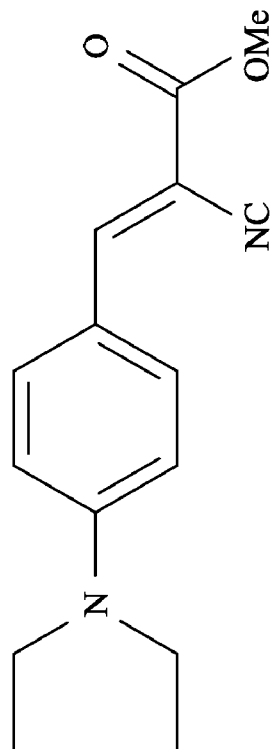
Figure 4C:
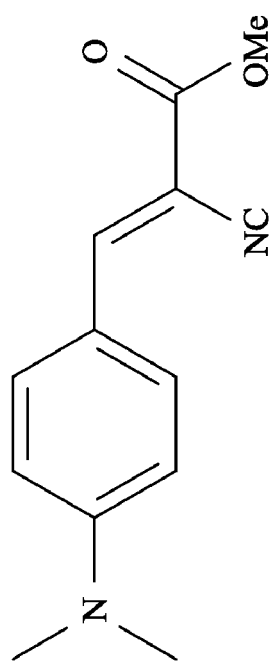
Figure 4D:
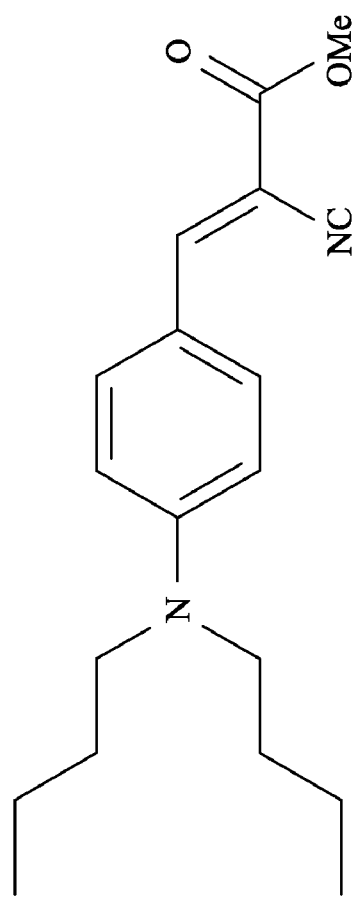

FIGS. 3A and 3B illustrate generic molecules that may act as a molecular rotor. A nitrogen atom is the electron donor for the intramolecular charge transfer, and the groups R2' and R2" are designed as electron acceptors. Exemplary acceptors are CN (nitrile), COOH (carboxylic acid), COOR (esters of carboxylic acid) and amides (CONR2). The carboxylic esters and/or amides may contain functionalities that may be used as attachment or recognition units to recognize substrates to which the probe is intended to attach. For example, the carboxylic ester group can contain functionalities that facilitate solubility in aqueous environments, such as biofluids, or lipophilic environments, such as the cell membrane. Similarly, antibodies may be used as the R2 group for recognizing a substrate.

FIGS. 3C through 3F illustrate additional generic molecules that may acts as molecular rotors in connection with the instant invention. In FIGS. 3C through 3F, R1 and R2 are preferably symmetric, and are designed to act as electron acceptors. While the groups that comprise R1 and R2 are contemplated to include a virtually unlimited number of possibilities, by way of example only, exemplary embodiments include FIGS. 3C through 3F where R1=R2=CH$_3$, R1=an NHS ester, any aliphatic chain (—[CH$_2$]$_n$—CH3), OH, a carboxy group (—COOH), esters to a carboxy group, to name a few. FIGS. 3 and 4 illustrate diols, and are advantageous in exposing two —OH groups to the environment. In one example, a silanization reaction could be used wherein one of either R1 or R2 is an NHS ester, and aminopropyltrioxysilane is used to attach to a glass surface and expose an NH$_2$ group. The NH$_2$ group reacts with the NHS to provide a covalent bond.

Specific exemplary molecules that may act as molecular rotors are illustrated in FIGS. 4A through 4H, which are, respectively, 9-(2-carboxy-2-cyanovinyl)-julolidine (CCVJ); 9-(2-carboxy-2-cyanovinyl)-julolidine triethyleneglycol ester (CCJV-TEG); 2-Cyano-3-(4-dimethylamino-phenyl)-acrylic acid methyl ester (DMCJ); 2-Cyano-3-(4-dibutylamino-phenyl)-acrylic acid methyl ester (SC1-20A); 2-Cyano-3-(4-diethylamino-phenyl)-acrylic acid methyl ester (SC1-40B); 2-Cyano-3-(4-diethylamino-2-pentyloxy-phenyl)-acrylic acid methyl ester (SC1-30B); 2-Cyano-3-(2-cyclohexylmethoxy-4-diethylamino-phenyl)-acrylic acid methyl ester (SC1-31B); and 9-(2,2-dicyanovinyl)-julolidine (DCVJ).

In an exemplary probe of the invention, a solid surface (e.g., quartz glass or polystyrene) is activated, and reacts with 8-(2-carboxy-2-cyanovinyl)julolidine, N-succimidyl ester. Thus, the rotors are covalently linked to the surface. In general, the invention is directed to molecular rotors bonded upon a surface that can be placed in a biofluid. Some particular applications will now be discussed to illustrate additional aspects and variations of the invention.

Figure 5:
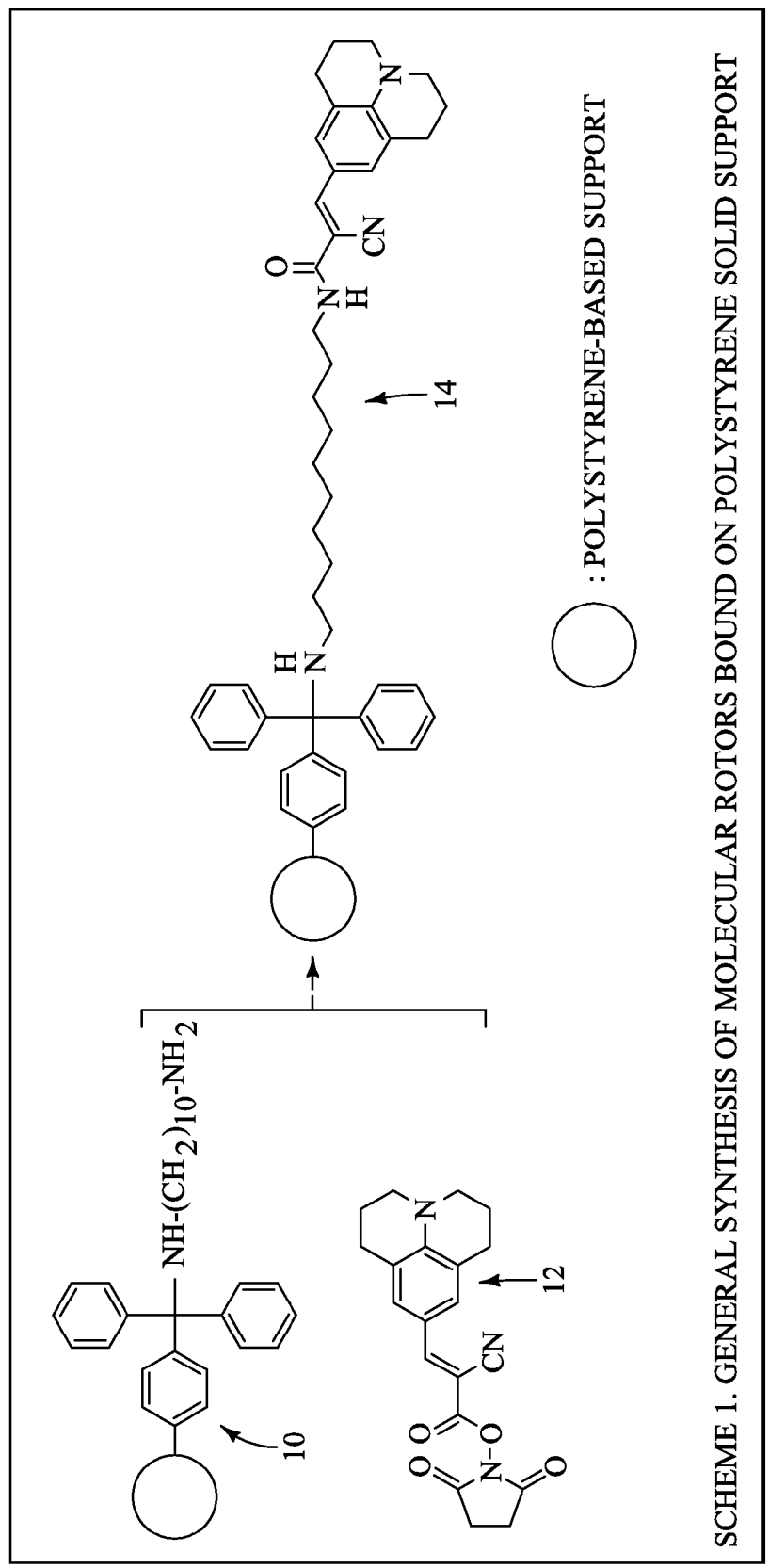
FIG. 5 is a schematic diagram illustrating a general synthesis of molecular rotors bound on polystyrene solid support.

Preparation of the preferred fiber optic tip may be based on commercially available polymeric supports, frequently employed in combinatorial chemistry. Polystyrene-based polymers, such as compound 10 in FIG. 5, for example, contain a reactive amine functionality, which may be used to graft the molecular rotor. The attachment may be performed using the succinimide derivative of the rotor of choice as the coupling reagent. The general coupling strategy to afford the molecular viscometer 14 is also illustrated in FIG. 5.

While the invention contemplates use of any solid-bound rotor having a polar group, exemplary rotors include solid-bound polar rotors having one of the structures illustrated in FIGS. 3A through 3F, where R2 is one of a COOH, OH, (CH$_2$O)$_n$CH$_3$, and O(CHOH)$_n$CH$_2$OH, and could be adhered to a fiber optic tip or other solid surface. In this application, a catheterized fiber optic probe would be inserted into a subject blood vessel, acquiring shear data at the site of insertion. For example, when inserted into the ventricles of the heart or at arterial bifurcations, shear data would be collected at those sites.

R1 would preferably be used as a reference moiety, wherein one R1 group is preferably fluorescent but not viscosity-sensitive. Intensity could be accurately calibrated by computing a ratio of rotor fluorescence to a reference fluorescence.

Figure 2:
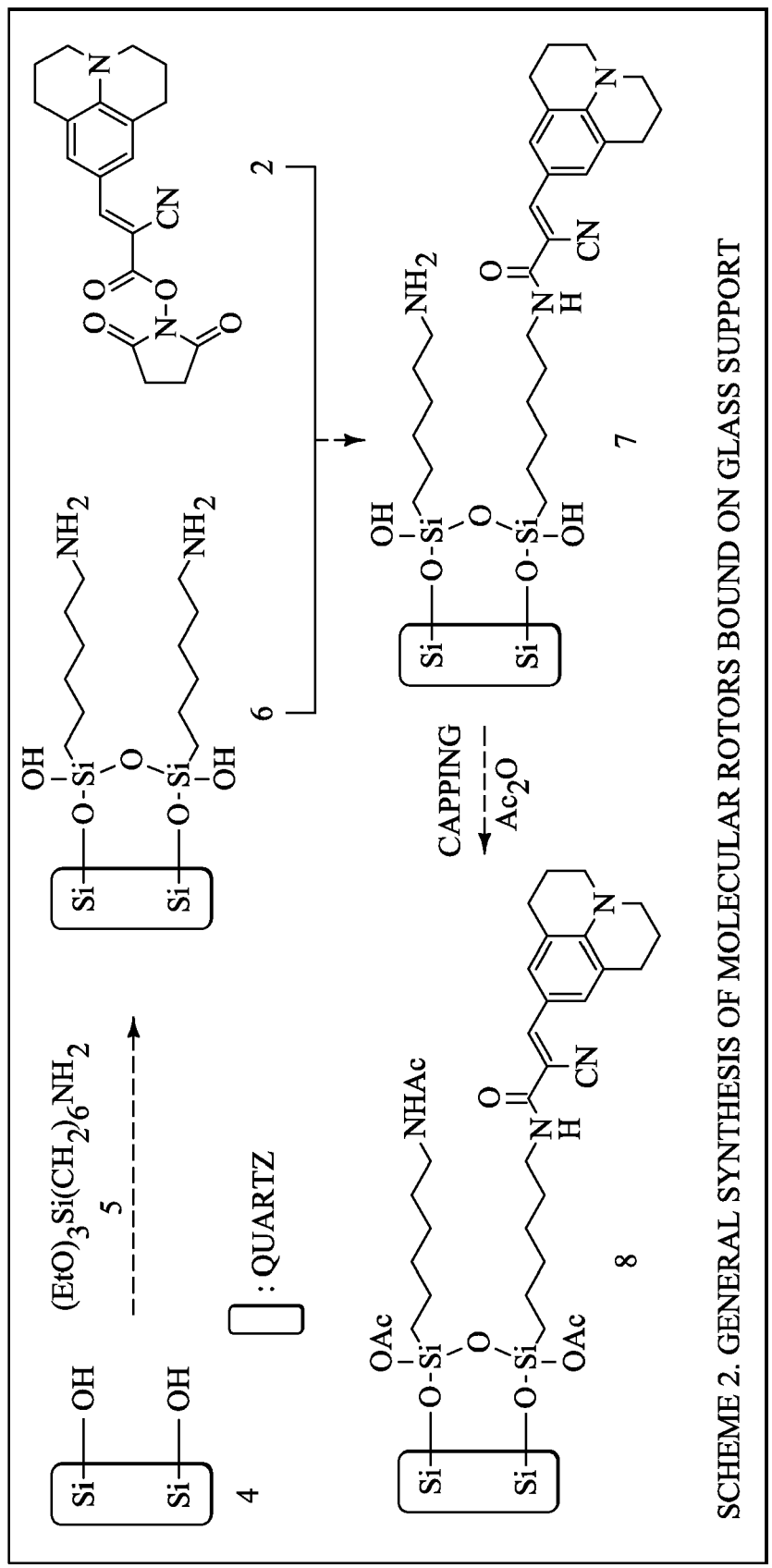
FIG. 2 is a schematic diagram illustrating a general synthesis of molecular rotors bound on glass support.

Viscosity-Sensitive Glass Surfaces for Both In Vivo and In Vitro Applications:

While it is contemplated that the invention may be used with receptacles such as glass or polymer tubes or microchannels, another preferred embodiment of the invention uses a glass cuvette, wherein one or more walls of a glass cuvette are covered with rotor molecules. As with the fiber optic probe, preparation of the glass cuvette and subsequent attachment of the molecular rotor(s) on the glass could be achieved on prefunctionalized silicate glass as illustrated in FIG. 2.

The viscosity of the boundary layer of any fluid in the cuvette can be measured using the principle of operation of a solid-bound molecular viscometer. Since the light path does not cross the fluid, it becomes independent of turbidity. While it is contemplated that as many as four walls of the cuvette may be treated, for exemplary purposes, the second preferred embodiment will be shown and described as having a single treated wall. For example, where one wall of a cuvette is treated, the cuvette will include one viscosity-sensitive wall. The fluid to be measured will then be filled into the cuvette and the fluorescence intensity measured. The measurement options are: a) comparative measurement to determine absolute viscosity using standard fluids; and b) timecourse measurement to determine viscosity changes over time.

Figure 6:
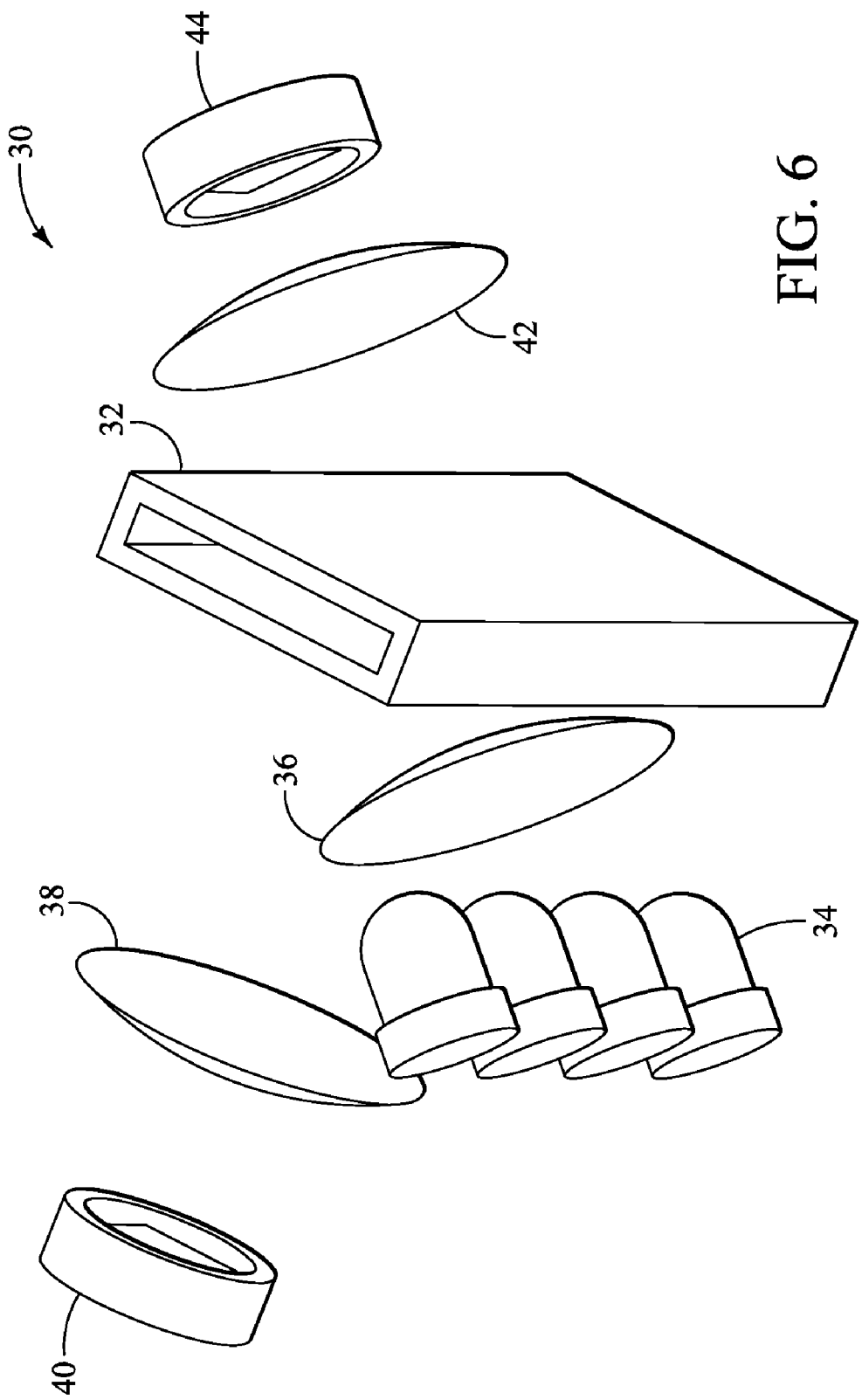
FIG. 6 is a schematic diagram illustrating the principle of operation of a solid-bound molecular viscometer.

More particularly, FIG. 6 illustrates the principle of the molecular viscometer, designated generally at 30, based on solid-bound probes in a cuvette 32. One wall of the glass or polystyrene cuvette 32 is covered with molecular rotors. The liquid to be measured will be filled into this cuvette 32. Excitation light is provided either by an excitation light source 34, such as mercury arc lamp, by a diode laser, or by an array of high-intensity blue light emitting diodes (LED). The relatively broad spectrum of these LEDs will be cut off at 475 nm and above by an excitation filter 36. An emission filter 38 is preferably a 10 nm bandwidth filter, which allows only the emission spectrum of the rotor to pass. An emission detector 40, such as a photomultiplier tube (PMT) or an avalanche photodiode (APD), amplifies the emission signal and feeds it into a computerized recording device (not shown). Optionally, an absorption filter 42 and collimating optics may be provided, as may be an absorption detector 44 (photodiode). The entire fluorescence group (LED array, cuvette, PMT, both filters) is housed in a light-proof cabinet, which may also be kept at a constant temperature. The advantage of emission LEDs over a mercury lamp lies in the fact that the energy consumption is low, which allows them to be battery-driven. Since the PMT 40 also has a lower power consumption, the entire device may be designed to be transportable and fed by rechargeable batteries.

Alternatively, a beamsplitter assembly is used to couple excitation light into the fiber and to collect emission light. A dichroic mirror is used to direct blue light from a light source onto the dichroic mirror and to reflect the blue light into the fiber. At a tip of the fiber, the excitation evanescent wave excites the rotors attached to the surface of the tip. As the emission light, which is the non-reflecting wavelength of the dichroic mirror, exits the fiber inside the measurement device, it passes the dichroic mirror. Scattered or otherwise leaked excitation light is further filtered with a filter positioned in front of the detector (photomultiplier tube, or PMT). The detector then quantitatively determines emission intensity.

Both viscosity-sensitive glass surfaces and rotor-covered fiber optic probes will have a wide range of applications in viscosity measurement (relative) and viscosity monitoring in the chemical and processing industry with the emphasis on fast read-outs and real-time measurements. There is a high demand for real-time viscometry in the biological and medical disciplines, specifically blood resuscitation medicine, and for clinical research as well. This is particularly valid for the in vivo probe of the invention. The use of disposable elements (disposable tips, disposable cuvettes) promotes the ease and simplicity of the application.

Proof of Principle and Experimental Results:

Glass surfaces have been covered with molecular rotors and measurements performed. A distinct emission peak matching that of free molecular rotors indicates the presence of covalently bound rotors on the surface. This fluorescence is resistant against different solvents (water, various alcohols). The glass slide exhibits this fluorescence when immersed in water. The presence of dextran in water increases the intensity of the emission peak, as illustrated in FIGS. 7A and 7B, which are graph illustrating two representative CCVJ spectra in low-viscosity and high-viscosity fluid (4 mPa s and 13.35 mPa s, respectively) with the fluorescein spectrum (dashed line) as a control. Specifically, Thorlabs multimode fibers (600 m core) were etched in hydrofluoric acid at room temperature for 30 minutes to form tapered tips. Aminopropyl trioxysilane (APS) was then used to activate the exposed surface. CCVJ-N-hydroxysuccinimidyl ester was brought to react with the APS-coated surface to form a covalent bond, thus immobilizing CCVJ to the glass surface of the fiberoptic tips. Using the same reaction, fluorescein was immobilized on different fibers to serve as non-rotor control. Epifluorescent microscopic examination clearly showed green fluorescence emitted from the rotor-coated tip. Both tips (fluorescein and CCVJ) were then exposed to water/dextran solutions of different concentration. Emission spectra were acquired, and the peak intensity was related to the viscosity of the dextran solutions in a double-logarithmic fashion to verify that emission intensity follows Equation 1:

$$\log \Phi = C + x \log \eta$$

From the plot of log intensity over log viscosity, it can clearly be seen that CCVJ emission intensity closely follows the Förster-Hoffmann relationship, while fluorescein does not show significant changes of intensity with viscosity. Thus, it is clear that immobilized molecular rotors retain their viscosity-sensitivity, and the value of solid-state fluorescent biosensors with molecular rotors linked to fiberoptics is evident.

Experiments: Materials, Methods and Results

Reagents obtained as follows: Fresh frozen human plasma was obtained from Interstate Blood Bank, INC., CCVJ from Helix Research, and CCVJ-TEG was synthesized. Fluoroscopy grade dimethyl sulfoxide (DMSO) was obtained from Sigma, Pentaspan (10% pentastarch in 0.9% NaCl, avg. MW 260 000) from B. Braun, Hetastarch (6% in 0.9% NaCl, avg. MW 670 000) from Abbott Laboratories. Dextran (80 000 average MW) from Sigma was used to prepare 5% solution in physiologic saline. Fluorescence spectroscopy was performed with samples in 4 mL clear methacrylate cuvettes using Spex Fluoromax-3. Absorbance measurements were made with a Beckman DU 520 spectrophotometer. Indices of refraction were taken with ATAGO R-5000 hand refractometer.

Fresh frozen plasma was thawed prior to use, then centrifuged at 180 g for 15 minutes and filtered through 75 mm 0.22 μm SFCA filter to remove cryoprecipitate. Post-processing protein concentration was determined by refractometry and confirmed by Lowry method. Crystalline dye was dissolved in DMSO to make 20 mM stock solutions of CCVJ and CCVJ-TEG. Sample viscosity was modulated by varying the amount of unstained plasma mixed with the starch plasma expanders dextran, hetastarch, and pentastarch. Plasma prestained with CCVJ or CCVJ-TEG (67 μM) was added in equal amounts to samples to minimize mixing errors. Final sample dye concentration was 13.3 μM. Three milliliters of each sample were transferred to 4 ml cuvettes and capped. All measurements were performed at room temperature (24° C.).

Calibration sets consisting of 5 different viscosities and 5 replicates each were made according to FIG. 8. A test set of 5 plasma-pentastarch mixtures, with different viscosity values than the calibration set, was made separately with 3 replicates each.

Figure 9:
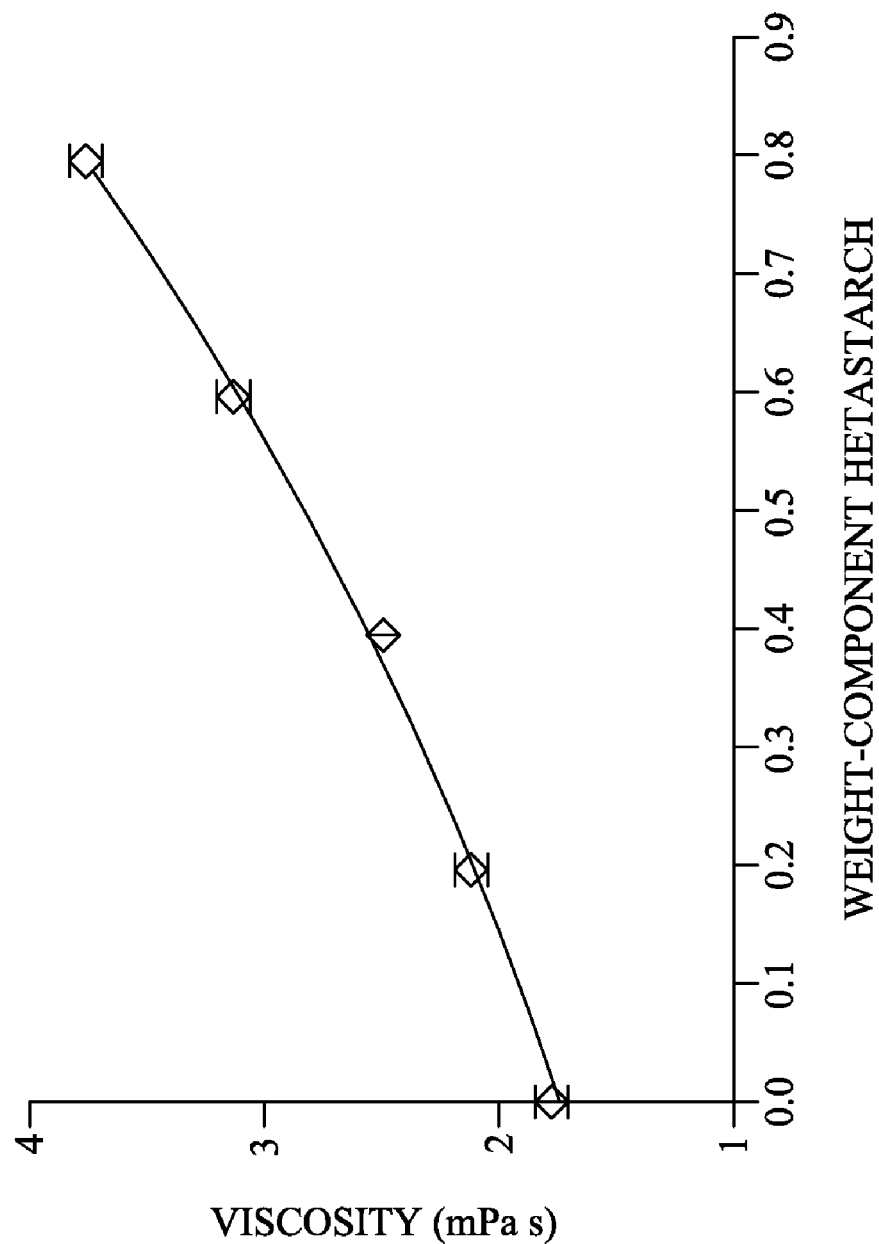
FIG. 9 is a graph illustrating a reference viscosity of plastma-hetastarch mixture computed from mechanically measured viscosity (data points)

Physical viscosity measurements for plasma mixtures were made with Brookfield DV-III+ cone-plate viscometer with CPE-40 spindle. Samples of 0.5 ml were measured at discrete shear rates: 150, 300, 450, 600, and 750 s$^{-1}$, (20, 40, 60, 80, and 100 rpm) in ramp-up, ramp-down series. Viscosity measurements were taken at 80 rpm (600 s−1). This shear rate was chosen to remain within instrument accuracy limits, and to reduce any apparent non-Newtonian effects on results. While noticeable instrument fluctuations as well as apparent shear-thinning effects existed at shear rates of 300 s$^{-1}$ and below, no visible influence of shear rate on measured viscosity existed at 450 s$^{-1}$ and above. Reference viscosity 0ref was computed for each plasma-plasma expander combination using Eq. 1:

$$\ln \eta_{ref} = \sum_{i=1}^{\eta} w_i \cdot \ln \eta_i$$

where $\eta_i$ is the viscosity of the individual component as measured by cone-plate viscometer and $w_i$ is the fractional amount of n=2 components, plasma and expander. The equation was verified and found to excellently described the plasma/expander mixtures, as represented in FIG. 9. Error bars indicate standard deviation.

The fluorescence emission intensity of each sample was measured from 470-530 nm at excitation wavelength of 440 nm for CCVJ, and 460 nm for CCVJ-TEG. Excitation and emission slits were 2 nm with integration time of 0.5 s. Peak intensity per sample was computed by averaging the emission intensity in a 5 nm window centered on the emission peak. Using the known relationship between viscosity q and quantum yield Φ of a molecular rotor, Equation 2:

$$\log \Phi = C + x \log \eta$$

which was solved for η, which yielded the fluorescence-based vicsosity $\eta_F$, as in Equation 3:

$$\eta_F = (\kappa \cdot \iota)^v$$

The constant $\kappa \alpha 10^{-C}$ relates quantum yield and dye concentration and $v=1/x$ describes the viscosity sensitivity of the molecular rotor. Constants κ and ν were determined from linear regression of log intensity over log viscosity for each plasma-expander calibration set. Deviation d of $\eta_F$ from $\eta_{ref}$ was computed using the following Equation 4:

$$d = 100 \cdot \frac{\eta_F - \eta_{ref}}{\eta_{ref}}$$

Fluorescence intensities of the test set samples were measured in the same manner as the calibration set. For each sample, $\eta_F$ was computed according to Eq. 3, using the constants κ and ν derived from the calibration set of plasma and pentastarch mixtures. The cone-plate rheometer was also used to measure sample viscosities. Deviation from $\eta_{ref}$ was calculated for both $\eta_F$ and rheometer results using Eq. 4.

Absorption measurements at 440 nm and 490 nm were used to normalize dye concentration between calibration set and individual test samples. A standard concentration factor was determined from the calibration set by linear regression of absorbance at 440 nm ($A_{440}$) versus absorbance at 490 nm ($A_{490}$), where the slope (χ) is related to plasma absorbance, and the intercept (β) is directly related to dye concentration. A normalization factor (Δ) was calculated for each sample according to Equation 5:

$$\Delta = \frac{A_{440} - X \cdot A_{490}}{\beta}$$

Normalized intensity was determined by multiplying measured sample intensity by the factor Δ.

Results

Cone-Plate Rheometer

Figure 10:
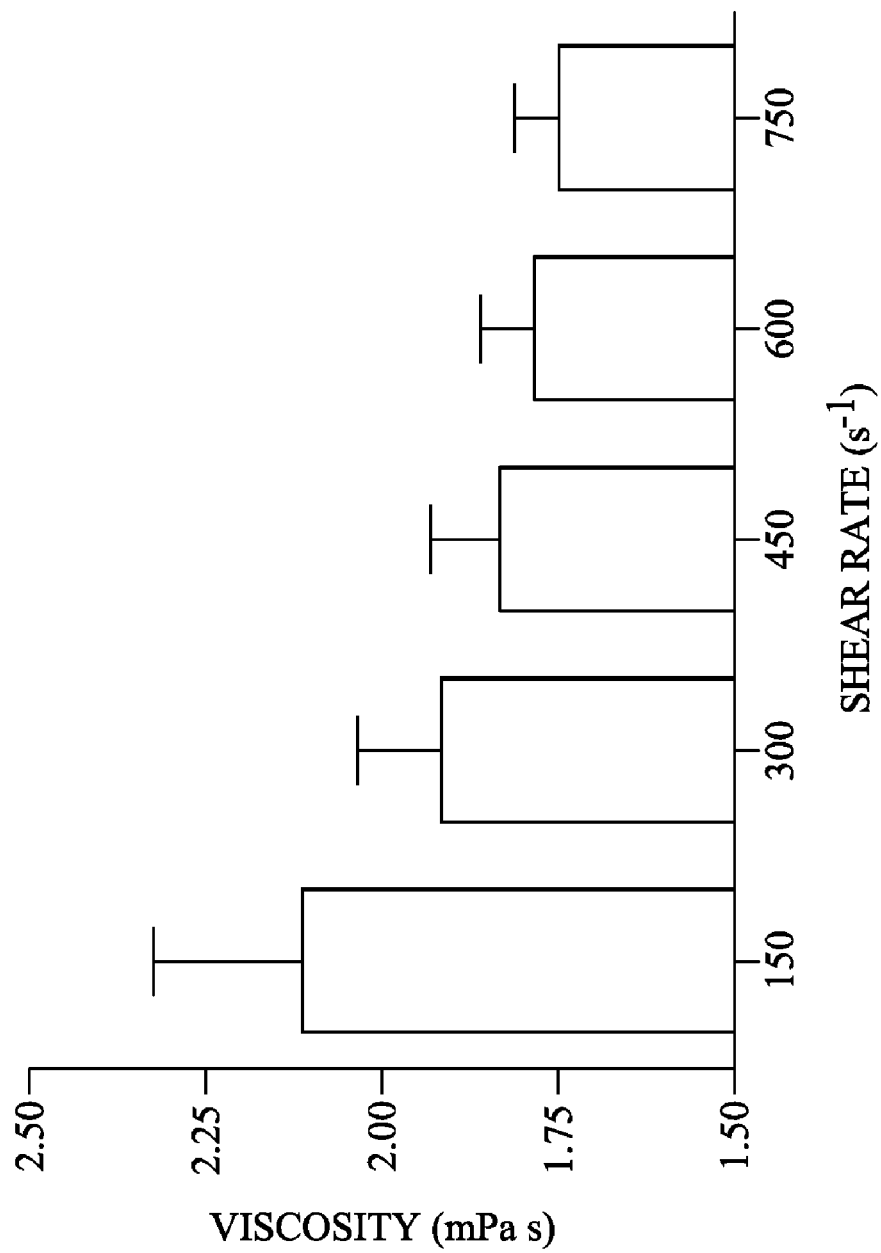
FIG. 10 is a graph illustrating the error analysis of blood plasma viscosity as measured using cone-plate rheometer at indicated shear rates.
Figure 11:
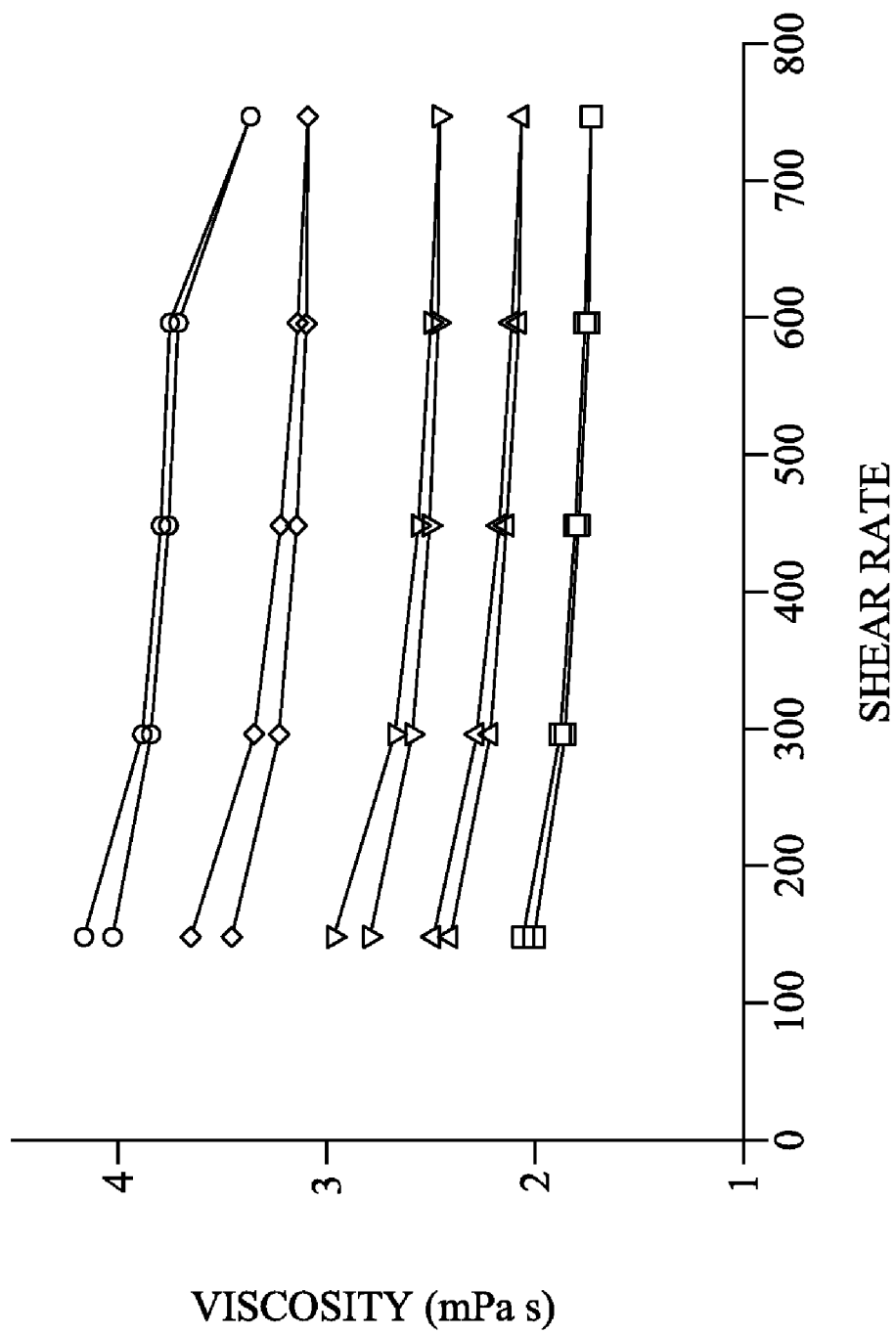
FIG. 11 is a graph illustrating viscosity values for plasma-hetastarch mixtures obtained with cone-and-plate rheometer at various shear rates using ramp-up, ramp-down protocol.

Physical viscosity values of human blood plasma at the shear rates used are represented in FIG. 10, with standard deviation shown by error bars. Deviation is lower and non-Newtonian behavior is minimal at higher shear rates. Viscosity curves for plasma-hetastarch mixtures are shown in FIG. 11 and are typical of all plasma-plasma expander mixtures. Deviations between viscosity measurements at 60 rpm and 100 rpm were less than 4% for plasma-hetastarch mixtures, 8% for plasma-dextran mixtures, and 5% for plasma-pentastarch mixtures. Highest viscosity solution exceeded instrument limits at 750 s⁻¹.

Refraction

Indices of refraction varied from 1.349 for pure plasma to 1.348 for pentastarch solution. According to Lakowicz, the correction factor is $(\eta_i/\eta_F)^2$, where $\eta_i$ is the refractive index of the sample and $\eta_F$ is the refractive index of air. This would lead to a difference of less than 0.15% of fluorescence intensity values between plasma and pentastarch solution. The influence of refractive index change was neglected in spectroscopic measurements.

Absorbance

Figure 12:
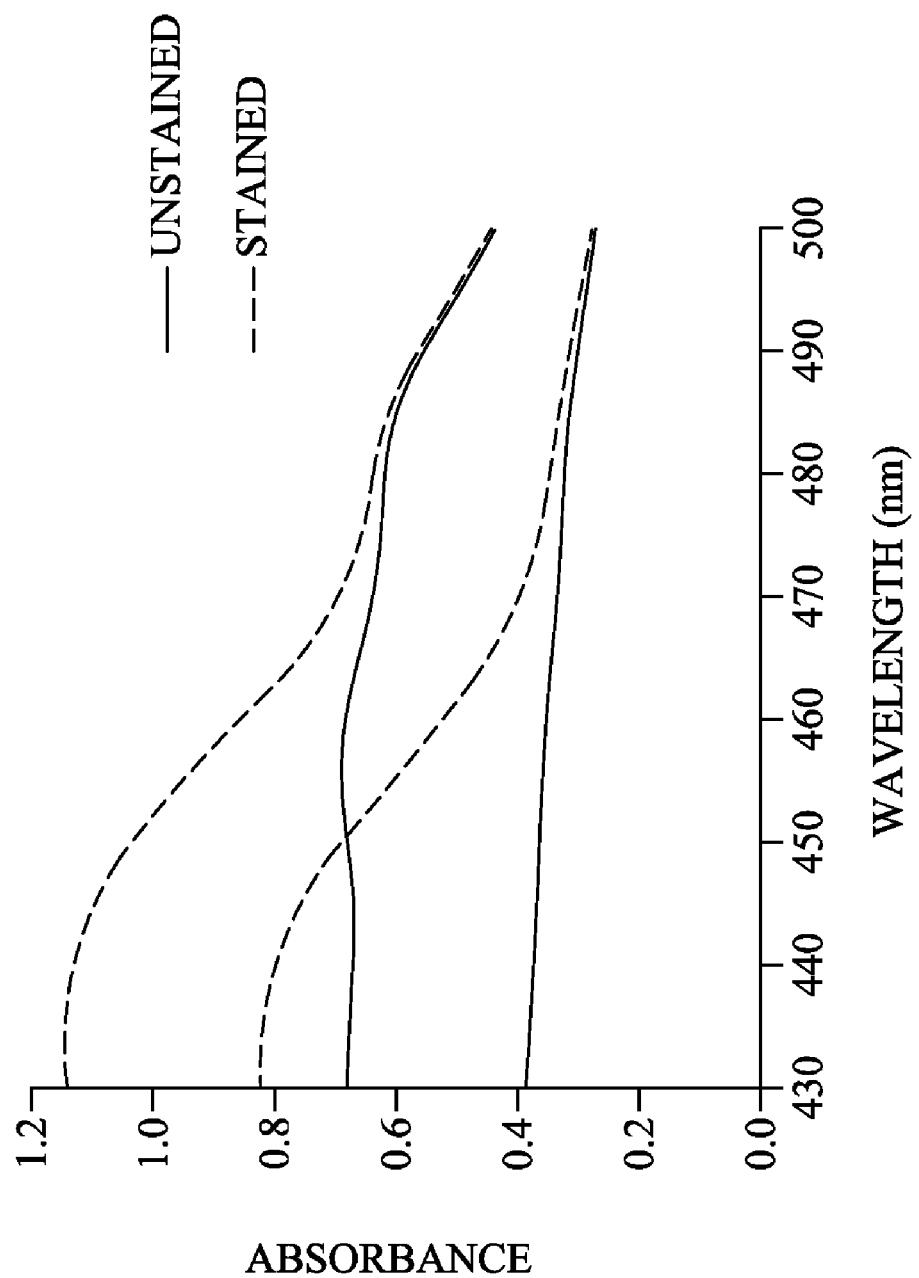
FIG. 12 is a graph illustrating the absorption spectra of CCVJ stained and unstained plasma-pentastarch mixtures.

FIG. 12 shows the absorption spectra of plasma and a plasma-pentastarch mixture with and without CCVJ. The contribution of the dye towards total absorbance is highest in the range of 430-450 nm, and is negligible at 490 nm and above. By measuring absorbance at the excitation peak of the dye (around 440 nm) and near the emission peak (490 nm), it is therefore possible to separate the contribution of the fluid and the dye towards total absorbance.

Molecular Rotor Fluorescence

Figure 13:
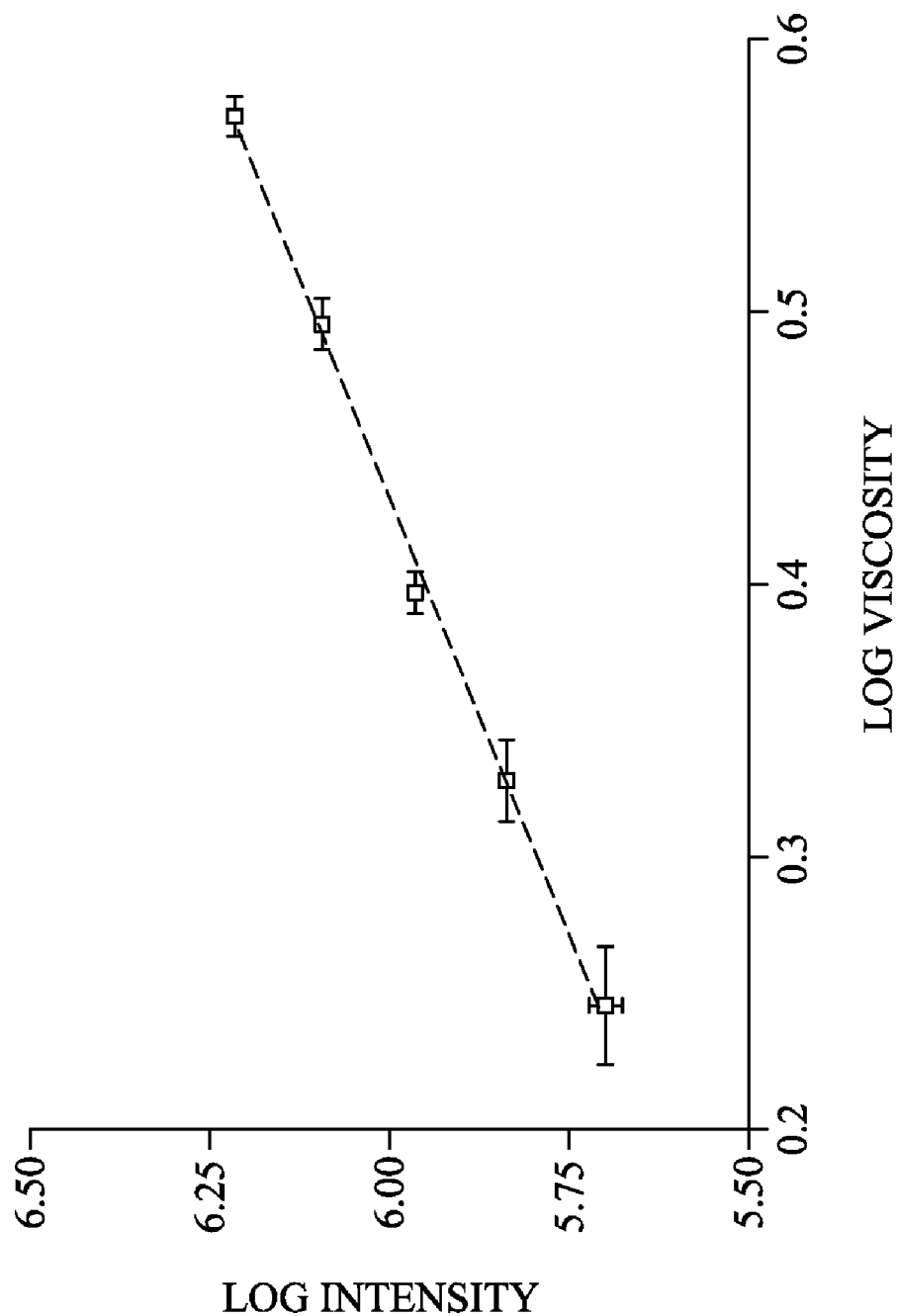
FIG. 13 is a graph illustrating log-log comparison of CCVJ fluorescence vs. plasma-hetastarch mixture viscosity.

Both CCVJ and CCVJ-TEG dissolved completely in the plasma mixtures. Plasma autofluorescence did not significantly affect fluorescence measurements at the dye concentration used in this study. Average wavelength of peak emission was 476 nm for CCVJ and 498 nm for CCVJ-TEG at excitation wavelength of 440 nm and 460 nm, respectively, with less than 5 nm deviation. FIG. 13 shows the comparison of log CCVJ fluorescence intensity to log plasma-hetastarch viscosity. Similar results were obtained for CCVJ and CCVJ-TEG in other plasma-plasma expander mixtures.

FIGS. 14 and 15 list the calibration constants κ and ν for Eq. 3 for the calibration sets stained with CCVJ and CCVJ-TEG, respectively. These tables also show that back-calculation of viscosity from molecular rotor fluorescence within the calibration set, using Eq. 3, resulted in deviation of less than 10% for all samples. With normalization of dye concentration (Eq. 5), deviation of $\eta_F$ was reduced to less than 6%. Coefficients of variation for mechanical and fluorescence viscosity measurements are compared in FIG. 16.

Figure 17:
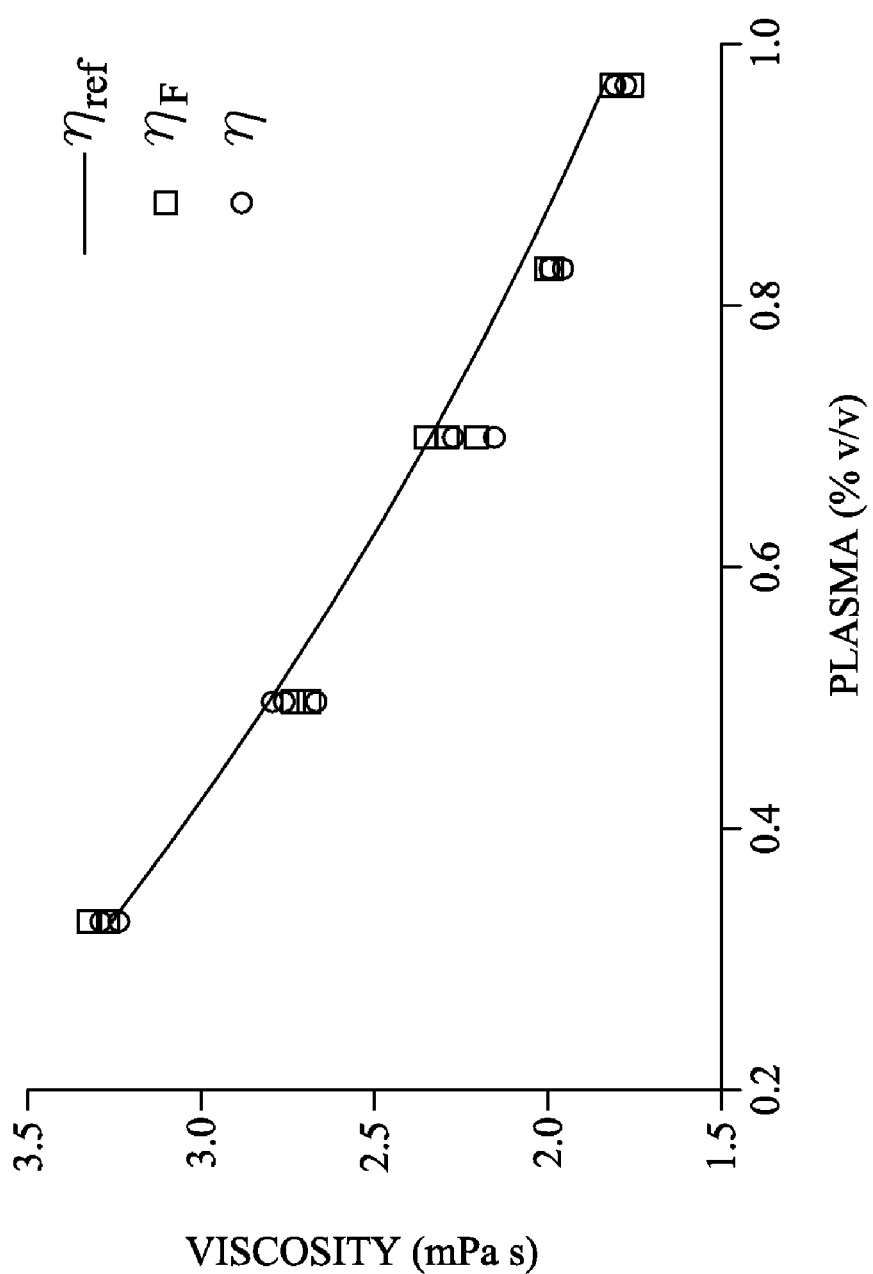
FIG. 17 is a graph illustrating a comparison of viscosity measurements made by cone-plate rehometer with fluorescence viscometry from calibration curve.

For the test set, viscosity determined by fluorescence $\eta_F$ of dissolved CCVJ in plasma-pentastarch mixtures was compared with values of $\eta_{ref}$ as determined by Eq. 1 for the plasma-pentastarch calibration set (FIG. 17). Maximum deviation for physical viscosity measurements using the cone-plate rheometer was 7.6%. Maximum deviation of 0F was less than 6%.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A method for measuring viscosity comprising:
   exposing a solid surface having molecular rotors attached thereto to a fluid having a viscosity to be measured; and
   taking optical measurements to determine viscosity.

2. The method of claim 1 further comprising a first step of attaching molecular rotors to a solid surface.

3. The method of claim 1 wherein the molecular rotors have a structure selected from the group consisting of:

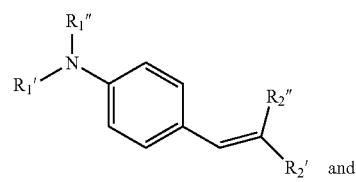

and

-continued

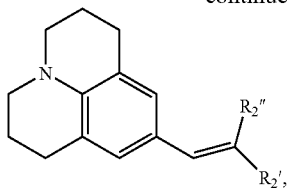

where at least one of R2, R2' and R2" is an electron acceptor.

4. The method of claim 3 wherein the electron acceptor is selected from the group consisting of CN, OH and a COOH.

5. The method of claim 1 wherein the molecular rotors have a structure selected from the group consisting of

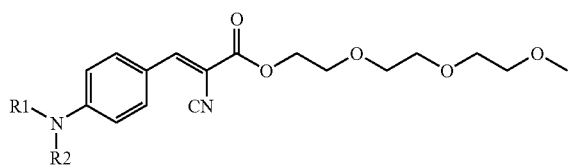

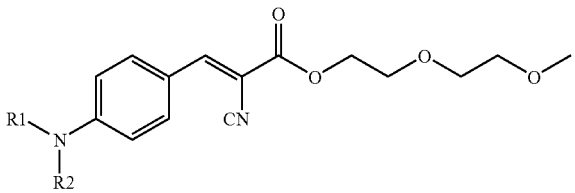

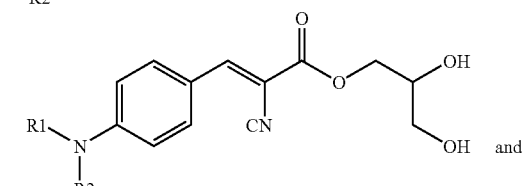

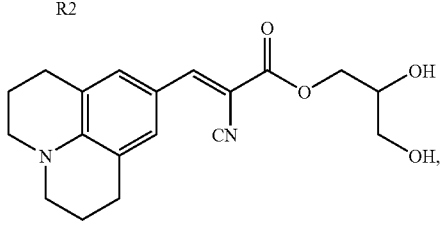

where R1 and R2 are symmetric and R1 is selected from the group consisting of R1=CH$_3$, an NHS ester, —[CH$_2$]$_n$—CH3, —OH, —COOH, and esters to a carboxy group.

6. The method of claim 1 wherein the molecular rotors are selected from the group consisting of CCVJ and CCVJ-TEG.

7. The method of claim 1 wherein the solid surface is composed of one of quartz, polystyrene and silicate glass.

8. The method of claim 1 wherein the solid surface is a tip of a fiber optic probe that is coupled to a fluorometer.

9. The method of claim 1 wherein the solid surface is at least one internal wall of a glass receptacle.

10. The method of claim 8 wherein the step of exposing the solid surface comprises inserting the tip of the fiber optic probe into the fluid.

11. The method of claim 8 further comprising catheterizing the tip of the fiber optic probe for in vivo insertion.

12. The method of claim 9 wherein the step of exposing the solid surface comprises placing the fluid in the glass receptacle.

13. The method of claim 1 wherein the step of taking optical measurements comprises measuring a fluorescence emission spectrum of the molecular rotors and correlating the spectrum to a viscosity.

14. The method of claim 1 further comprising calibrating signal intensity by computing a ratio of rotor fluorescence value to a reference fluorescence value.

15. The method of claim 1 further comprising measuring an excited-state lifetime to obtain quantum yield.

16. An in vivo or in vitro method of measuring biofluid viscosity comprising:
    providing a fiber optic probe having a fiber optic tip;
    adhering molecular rotors to the fiber optic tip;
    inserting the fiber optic tip into a predetermined environment containing a biofluid; and
    measuring fluorescence though the fiber.

17. The method of claim 16 wherein the molecular rotors have a structure selected from the group consisting of

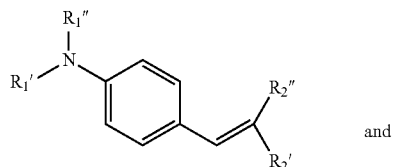

and

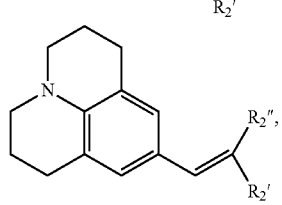

where at least one of R2, R2' and R2" is an electron acceptor.

18. The method of claim 16 wherein the electron acceptor is selected from the group consisting of CN, OH and a COOH.

19. The method of claim 16 wherein the molecular rotors have a structure selected from the group consisting of:

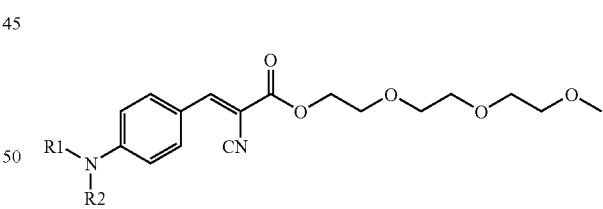

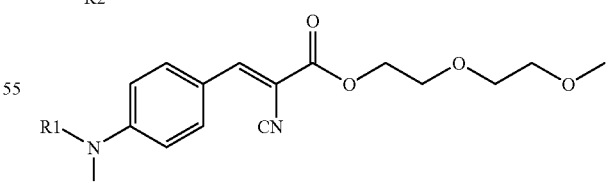

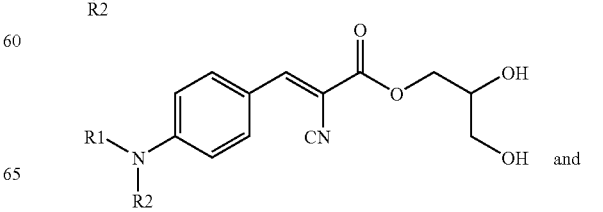

and

-continued

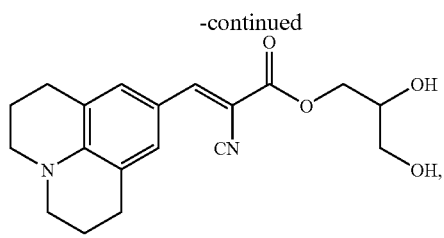

where R1 and R2 are symmetric and R1 is selected from the group consisting of R1=CH$_3$, an NHS ester, —[CH$_2$]$_n$—CH3, —OH, —COOH, and esters to a carboxy group.

20. The method of claim 16 wherein the molecular rotors are selected from the group consisting of CCVJ and CCVJ-TEG.

21. The method of claim 16 further comprising catheterizing the probe tip.

22. The method of claim 21 wherein the predetermined environment is a blood vessel.

23. The method of claim 16 further comprising coupling the fiber optic probe to a fluorometer.

* * * * *

UNITED STATES PATENT AND TRADEMARK OFFICE
CERTIFICATE OF CORRECTION

PATENT NO. : 7,943,390 B2
APPLICATION NO. : 12/426653
DATED : May 17, 2011
INVENTOR(S) : Haidekker et al.

It is certified that error appears in the above-identified patent and that said Letters Patent is hereby corrected as shown below:

In the Specification:

| | |
|---|---|
| Col. 1, line 50 | Delete "sever" and insert --severe-- therefor. |
| Col. 3, line 25 | Delete "rehometer" and insert --rheometer-- therefor. |
| Col. 7, line 51 | Before "illustrating" delete "graph" and insert --graphs-- therefor. |
| Col. 9, line 7 | Delete "viscosity q" and insert --viscosity $\eta$-- therefor. |

In the Claims:

| | |
|---|---|
| Col. 12, line 17 Claim 16, line 7 | After "fluorescence" delete "though" and insert --through-- therefor. |

Signed and Sealed this
Eleventh Day of October, 2011

David J. Kappos
*Director of the United States Patent and Trademark Office*